United States Patent
Baker et al.

(10) Patent No.: US 10,369,308 B2
(45) Date of Patent: *Aug. 6, 2019

(54) FEATURE SYNCHRONIZATION SYSTEM AND METHOD FOR ELECTRONIC VAPOR PROVISION SYSTEMS

(71) Applicant: Nicoventures Holdings Limited, London (GB)

(72) Inventors: Darryl Baker, London (GB); Ross Oldbury, London (GB)

(73) Assignee: Nicoventures Holdings Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/764,218

(22) PCT Filed: Sep. 14, 2016

(86) PCT No.: PCT/GB2016/052832
§ 371 (c)(1),
(2) Date: Mar. 28, 2018

(87) PCT Pub. No.: WO2017/055803
PCT Pub. Date: Apr. 6, 2017

(65) Prior Publication Data
US 2018/0280640 A1    Oct. 4, 2018

(30) Foreign Application Priority Data
Sep. 28, 2015   (GB) .................................. 1517094.7

(51) Int. Cl.
*A61M 15/06*    (2006.01)
*G08B 5/36*    (2006.01)
(Continued)

(52) U.S. Cl.
CPC .......... *A61M 15/06* (2013.01); *A24F 47/008* (2013.01); *G08B 5/36* (2013.01);
(Continued)

(58) Field of Classification Search
CPC ............................................ A61M 2016/0024
See application file for complete search history.

(56) References Cited

U.S. PATENT DOCUMENTS 9,833,020 B2 * 12/2017 Shabat ................... H04M 1/21
2007/0014314 A1   1/2007 O'Neil
(Continued)

FOREIGN PATENT DOCUMENTS

| CN | 103798960 A | 5/2014 |
| CN | 203913385 U | 11/2014 |

(Continued)

OTHER PUBLICATIONS

Application and File History for U.S. Appl. No. 15/764,223, filed Mar. 28, 2018, Inventors: Baker et al.
(Continued)

*Primary Examiner* — John F Mortell
(74) *Attorney, Agent, or Firm* — Patterson Thuente Pedersen, P.A.

(57) ABSTRACT

A method of synchronizing a feature between an electronic vapor provision system and a mobile communication device of a user includes obtaining a current parameter of a configurable feature on one of the electronic vapor provision system and the mobile communication device; communicating an indication of the parameter to the other of the electronic vapor provision system and the mobile communication device; and the other one of the electronic vapor provision system and the mobile communication device reconfiguring a corresponding feature in response to the communicated indication of the parameter.

11 Claims, 9 Drawing Sheets

(51) Int. Cl.
*A24F 47/00* (2006.01)
*H04L 12/24* (2006.01)
*A61M 16/00* (2006.01)

(52) U.S. Cl.
CPC .............. *A61M 2016/0024* (2013.01); *A61M 2016/0027* (2013.01); *A61M 2205/3331* (2013.01); *A61M 2205/3368* (2013.01); *A61M 2205/3561* (2013.01); *A61M 2205/3584* (2013.01); *A61M 2205/3592* (2013.01); *A61M 2205/3653* (2013.01); *A61M 2205/505* (2013.01); *A61M 2205/581* (2013.01); *A61M 2205/587* (2013.01); *A61M 2205/6018* (2013.01); *A61M 2205/8206* (2013.01); *A61M 2205/8243* (2013.01); *H04L 41/08* (2013.01)

(56) References Cited

U.S. PATENT DOCUMENTS

| | | | |
|---|---|---|---|
| 2011/0265806 A1 | 11/2011 | Alarcon | |
| 2013/0276799 A1 | 10/2013 | Davidson | |
| 2013/0284192 A1* | 10/2013 | Peleg | A24F 47/002 131/329 |
| 2013/0319439 A1* | 12/2013 | Gorelick | A24F 47/008 131/329 |
| 2013/0340775 A1* | 12/2013 | Juster | H04L 67/42 131/273 |
| 2014/0107815 A1* | 4/2014 | LaMothe | A24F 15/18 700/90 |
| 2014/0123990 A1* | 5/2014 | Timmermans | A24F 47/0008 131/328 |
| 2014/0174459 A1 | 6/2014 | Burstyn | |
| 2014/0202477 A1* | 7/2014 | Qi | A24F 47/008 131/329 |
| 2015/0075546 A1* | 3/2015 | Kueny, Sr. | A24F 47/008 131/329 |
| 2015/0101625 A1* | 4/2015 | Newton | H05B 1/0244 131/329 |
| 2015/0181945 A1* | 7/2015 | Tremblay | A24F 47/008 131/328 |
| 2015/0304401 A1* | 10/2015 | Liu | A24F 47/008 709/217 |
| 2015/0304402 A1* | 10/2015 | Liu | A24F 47/008 709/203 |
| 2016/0278435 A1* | 9/2016 | Choukroun | A24F 47/008 |
| 2017/0048691 A1 | 2/2017 | Liu | |
| 2017/0118292 A1 | 4/2017 | Xiang | |
| 2017/0118584 A1 | 4/2017 | Xiang | |

FOREIGN PATENT DOCUMENTS

| | | |
|---|---|---|
| EP | 1111527 A2 | 6/2001 |
| GB | 2519317 A | 4/2015 |
| RU | 103281 | 4/2011 |
| WO | WO9406314 | 3/1994 |
| WO | WO2013083635 | 6/2013 |
| WO | WO2014150704 A2 | 9/2014 |
| WO | WO2014195805 A2 | 12/2014 |
| WO | WO2014199233 A2 | 12/2014 |
| WO | WO2014205456 A2 | 12/2014 |
| WO | WO2015119918 A1 | 8/2015 |
| WO | WO2015161485 | 10/2015 |
| WO | WO2016008096 A1 | 1/2016 |
| WO | WO2015063126 A1 | 5/2016 |

OTHER PUBLICATIONS

Russian Decision to Grant, Application No. 2018110806, dated Nov. 30, 2018, 10 pages.
Russian Search Report, Application No. 2018110806, dated Nov. 30, 2018, 2 pages.
New Zealand Examination Report, Application No. 740653, dated Sep. 13, 2018, 4 pages.
International Search Report and Written Opinion, Application No. PCT/GB2016/052832, dated Nov. 24, 2016, 12 pages.
International Preliminary Report on Patentability, Application No. Application No. PCT/GB2016/052832, dated Sep. 20, 2017, 15 pages.
Great Britain Search Report, Application No. GB1517094.7, dated Feb. 23, 2016, 4 pages.
Dialog, *DA14580 Low Power Bluetooth Smart SoC*. As available at: http://www.dialog-semiconductor.com/products/bluetooth-smart/smartbond-da14580. Jan. 29, 2015, dated Jan. 29, 2015, vol. 3.1, 158 pages.
IEEE, 802.15.1 (Jun. 14, 2002) *IEEE Standard for Telecommunications and Information Exchange Between Systems—LAN/MAN—Specific Requirements Part 15: Wireless Medium Access Control (MAC) and Physical Layer (PHY) Specifications for Wireless Personal Area Networks (WPANs)*, 2 pages.
IEEE, *802.11ah IEEE Draft Standard for Information Technology-Telecommunications and Information Exchange between Systems—Local and Metropolitan Area networks—Specific Requirements—Part 11: Wireless LAN Medium Access Control (MAC) and Physical Layer* (Feb. 2016), 2 pages.
IEEE, *IEEE Publishes the 802.11v Amendment Titled Wireless Network Management to Extend the Base IEEE 802.11 ™ Wireless LAN Standards* (May 13, 2011), 1 page.
ISO *13157-1: 2014 Information Technology—Telecommunications and information exchange between systems—NFC Security Part 1 NFC-SEC NFCIP-1 security services and protocol* (Aug. 15, 2014), 2 pages.
Bluetooth, *Bluetooth Smart Technology: Powering the Internet of things*, as available at http://www.bluetooth.com/Pages/Bluetooth-Smart.aspx (Nov. 10, 2014), 2 pages.
Great Britain Search Report, Application No. GB1517092.1, dated Feb. 22, 2016, 3 pages.
International Preliminary Report on Patentability, Application No. PCT/GB2016/052831, dated Sep. 8, 2017, 8 pages.
International Search Report and Written Opinion, Application No. PCT/GB2016/052831, dated Nov. 29, 2016, 13 pages.
Japanese Notice of Allowance, Application No. 2018-516004, dated Mar. 12, 2019, 3 pages (6 pages with translation).

* cited by examiner

FEATURE SYNCHRONIZATION SYSTEM AND METHOD FOR ELECTRONIC VAPOR PROVISION SYSTEMS

PRIORITY CLAIM

The present application is a National Phase entry of PCT Application No. PCT/GB2016/052832, filed Sep. 14, 2016, which claims priority from GB Patent Application No. 1517094.7, filed Sep. 28, 2015, each of which is hereby fully incorporated herein by reference.

FIELD

The present disclosure relates to a feature synchronization system and method for electronic vapor provision systems such as electronic nicotine delivery systems (e.g. e-cigarettes).

BACKGROUND

Electronic vapor provision systems, such as e-cigarettes and other aerosol delivery systems, generally contain a reservoir of liquid which is to be vaporized, typically nicotine (this is sometimes referred to as an "e-liquid"). When a user inhales on the device, an electrical (e.g. resistive) heater is activated to vaporize a small amount of liquid, in effect producing an aerosol which is therefore inhaled by the user. The liquid may comprise nicotine in a solvent, such as ethanol or water, together with glycerine or propylene glycol to aid aerosol formation, and may also include one or more additional flavors. The skilled person will be aware of many different liquid formulations that may be used in e-cigarettes and other such devices.

The practice of inhaling vaporized liquid in this manner is commonly known as "vaping."

An e-cigarette may have an interface to support external data communications. This interface may be used, for example, to load control parameters and/or updated software onto the e-cigarette from an external source. Alternatively or additionally, the interface may be utilized to download data from the e-cigarette to an external system. The downloaded data may, for example, represent usage parameters of the e-cigarette, fault conditions, etc. As the skilled person will be aware, many other forms of data can be exchanged between an e-cigarette and one or more external systems (which may be another e-cigarette).

In some cases, the interface for an e-cigarette to perform communication with an external system is based on a wired connection, such as a USB link using a micro, mini, or ordinary USB connection into the e-cigarette. The interface for an e-cigarette to perform communication with an external system may also be based on a wireless connection. Such a wireless connection has certain advantages over a wired connection. For example, a user does not need any additional cabling to form such a connection. In addition, the user has more flexibility in terms of movement, setting up a connection, and the range of pairing devices.

Note that many e-cigarettes already provide support for a USB interface in order to allow the e-cigarette to be re-charged. Accordingly, the additional use of such a wired interface to also provide data communications is relatively straightforward. However, the situation for providing a wireless data connection is more complex.

SUMMARY

In one aspect of the present disclosure, there is provided a method of synchronizing a feature between an electronic vapor provision system and a mobile communication device of a first user.

In another aspect of the present disclosure, there is provided an electronic vapor provision system.

In another aspect of the present disclosure, there is provided a mobile communication device.

Further respective aspects and features of the disclosure are defined in the appended claims.

BRIEF DESCRIPTION OF THE DRAWINGS

Embodiments of the present disclosure will now be described by way of example with reference to the accompanying drawings, in which.

DETAILED DESCRIPTION

A feature synchronization system and method for electronic vapor provision systems are disclosed. In the following description, a number of specific details are presented in order to provide a thorough understanding of certain example implementations of apparatus and methods according to the present disclosure. It will be apparent, however, to a person skilled in the art that these specific details need not be employed in all implementations. Conversely, specific details known to the person skilled in the art are omitted for the purposes of clarity where appropriate.

As described above, the present disclosure relates to an electronic vapor provision system, such as an e-cigarette. Throughout the following description the term "e-cigarette" is used; however, this term may be used interchangeably with electronic vapor provision system, aerosol delivery device, and other similar terminology.

Figure 1:
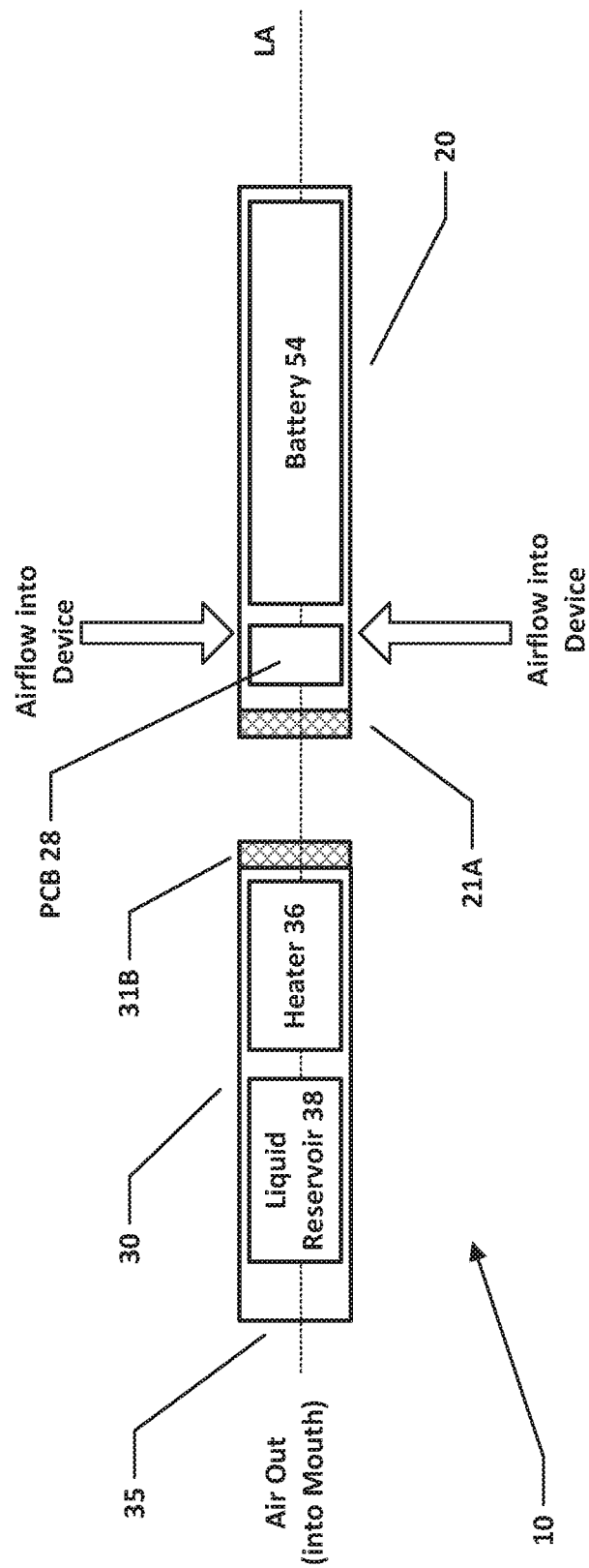
FIG. 1 is a schematic (exploded) diagram of an e-cigarette in accordance with some embodiments of the disclosure.

FIG. 1 is a schematic (exploded) diagram of an e-cigarette 10 in accordance with some embodiments of the disclosure (not to scale). The e-cigarette 10 comprises a body or control unit 20 and a cartomizer 30. The cartomizer 30 includes a reservoir 38 of liquid, typically including nicotine, a heater 36, and a mouthpiece 35. The e-cigarette 10 has a longitudinal or cylindrical axis which extends along the center-line of the e-cigarette 10 from the mouthpiece 35 at one end of the cartomizer 30 to the opposing end of the control unit 20 (usually referred to as the tip end). This longitudinal axis is indicated in FIG. 1 by the dashed line denoted LA.

The liquid reservoir 38 in the cartomizer 30 may hold the (e-)liquid directly in liquid form, or may utilize some absorbing structure, such as a foam matrix or cotton material, etc, as a retainer for the liquid. The liquid is then fed from the reservoir 38 to be delivered to a vaporizer comprising the heater 36. For example, liquid may flow via capillary action from the reservoir 38 to the heater 36 via a wick (not shown in FIG. 1).

In other devices, the liquid may be provided in the form of plant material or some other (ostensibly solid) plant derivative material. In this case the liquid can be considered as representing volatiles in the material which vaporize when the material is heated. Note that devices containing this type of material generally do not require a wick to transport the liquid to the heater, but rather provide a suitable arrangement of the heater in relation to the material to provide suitable heating.

The control unit 20 includes a re-chargeable cell or battery 54 to provide power to the e-cigarette 10 (referred to hereinafter as a battery) and a printed circuit board (PCB) 28 and/or other electronics for generally controlling the e-cigarette 10.

The control unit 20 and the cartomizer 30 are detachable from one another, as shown in FIG. 1, but are joined together when the device 10 is in use, for example, by a screw or bayonet fitting. The connectors on the cartomizer 30 and the control unit 20 are indicated schematically in FIG. 1 as 31B and 21A respectively. This connection between the control unit 20 and cartomizer 30 provides for mechanical and electrical connectivity between the two.

When the control unit 20 is detached from the cartomizer 30, the electrical connection 21A on the control unit 20 that is used to connect to the cartomizer 30 may also serve as a socket for connecting a charging device (not shown). The other end of this charging device can be plugged into a USB socket to re-charge the battery 54 in the control unit 20 of the e-cigarette 10. In other implementations, the e-cigarette 10 may be provided (for example) with a cable for direct connection between the electrical connection 21A and a USB socket.

The control unit 20 is provided with one or more holes for air inlet adjacent to PCB 28. These holes connect to an air passage through the control unit to an air passage provided through the connector 21A. This then links to an air path through the cartomizer 30 to the mouthpiece 35. Note that the heater 36 and the liquid reservoir 38 are configured to provide an air channel between the connector 31B and the mouthpiece 35. This air channel may flow through the center of the cartomizer 30, with the liquid reservoir 38 confined to an annular region around this central path. Alternatively (or additionally) the airflow channel may lie between the liquid reservoir 38 and an outer housing of the cartomizer 30.

When a user inhales through the mouthpiece 35, air is drawn into the control unit 20 through the one or more air inlet holes. This airflow (or the associated change in pressure) is detected by a sensor, e.g. a pressure sensor, which in turn activates the heater 36 to vaporize the nicotine liquid fed from the reservoir 38. The airflow passes from the control unit 20 into the vaporizer, where the airflow combines with the nicotine vapor. This combination of airflow and nicotine vapor (in effect, an aerosol) then passes through the cartomizer 30 and out of the mouthpiece 35 to be inhaled by a user. The cartomizer 30 may be detached from the control unit 20 and disposed of when the supply of nicotine liquid is exhausted (and then replaced with another cartomizer).

It will be appreciated that the e-cigarette 10 shown in FIG. 1 is presented by way of example only, and many other implementations may be adopted. For example, in some implementations, the cartomizer 30 is split into a cartridge containing the liquid reservoir 38 and a separate vaporizer portion containing the heater 36. In this configuration, the cartridge may be disposed of after the liquid in reservoir 38 has been exhausted, but the separate vaporizer portion containing the heater 36 is retained. Alternatively, an e-cigarette may be provided with a cartomizer 30 as shown in FIG. 1, or else constructed as a one-piece (unitary) device, but the liquid reservoir 38 is in the form of a (user-)replaceable cartridge. Further possible variations are that the heater 36 may be located at the opposite end of the cartomizer 30 from that shown in FIG. 1, i.e. between the liquid reservoir 38 and the mouthpiece 35, or else the heater 36 is located along a central axis LA of the cartomizer, and the liquid reservoir is in the form of an annular structure which is radially outside the heater 36.

The skilled person will also be aware of a number of possible variations for the control unit 20. For example, airflow may enter the control unit 20 at the tip end, i.e. the opposite end to connector 21A, in addition to or instead of the airflow adjacent to PCB 28. In this case the airflow would typically be drawn towards the cartomizer 30 along a passage between the battery 54 and the outer wall of the control unit 20. Similarly, the control unit 20 may comprise a PCB located on or near the tip end, e.g. between the battery 54 and the tip end. Such a PCB may be provided in addition to or instead of PCB 28.

Furthermore, an e-cigarette 10 may support charging at the tip end, or via a socket elsewhere on the device, in addition to or in place of charging at the connection point between the cartomizer 30 and the control unit 20. (It will be appreciated that some e-cigarettes are provided as essentially integrated units, in which case a user is unable to disconnect the cartomizer 30 from the control unit 20.) Other e-cigarettes may also support wireless (induction) charging, in addition to (or instead of) wired charging.

The above discussion of potential variations to the e-cigarette 10 shown in FIG. 1 is by way of example. The skilled person will aware of further potential variations (and combination of variations) for the e-cigarette 10.

Figure 2:
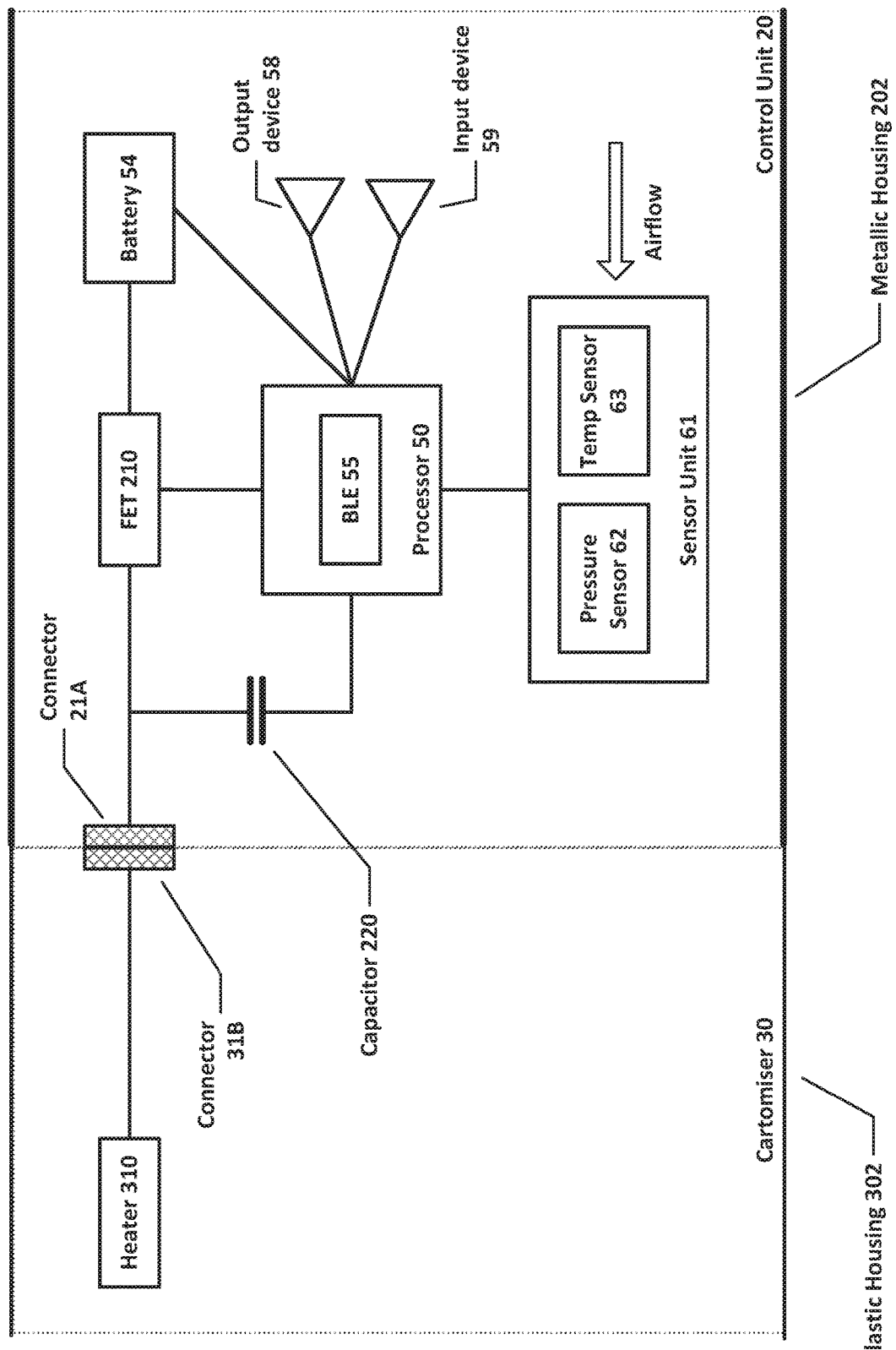
FIG. 2 is a schematic diagram of the main electrical/electronic components of the e-cigarette of FIG. 1 in accordance with some embodiments of the disclosure.

FIG. 2 is a schematic diagram of the main functional components of the e-cigarette 10 of FIG. 1 in accordance with some embodiments of the disclosure. N.B. FIG. 2 is primarily concerned with electrical connectivity and functionality—it is not intended to indicate the physical sizing of the different components, nor details of their physical placement within the control unit 20 or cartomizer 30. In addition, it will be appreciated that at least some of the components shown in FIG. 2 located within the control unit 20 may be mounted on the circuit board 28. Alternatively, one or more of such components may instead be accommodated in the control unit 20 to operate in conjunction with the circuit board 28, but not physically mounted on the circuit board 28 itself. For example, these components may be located on one or more additional circuit boards, or they may be separately located (such as battery 54).

As shown in FIG. 2, the cartomizer 30 contains heater 310 which receives power through connector 31B. The control unit 20 includes an electrical socket or connector 21A for connecting to the corresponding connector 31B of the cartomizer 30 (or potentially to a USB charging device). This then provides electrical connectivity between the control unit 20 and the cartomizer 30.

The control unit 20 further includes a sensor unit 61, which is located in or adjacent to the air path through the control unit 20 from the air inlet(s) to the air outlet (to the cartomizer 30 through the connector 21A). The sensor unit 61 contains a pressure sensor 62 and temperature sensor 63 (also in or adjacent to this air path). The control unit 20 further includes a capacitor 220, a processor 50, a field effect transistor (FET) switch 210, a battery 54, and input and output devices 59, 58.

The operations of the processor 50 and other electronic components, such as the pressure sensor 62, are generally controlled at least in part by software programs running on the processor 50 (or other components). Such software programs may be stored in non-volatile memory, such as ROM, which can be integrated into the processor 50 itself, or provided as a separate component. The processor 50 may access the ROM to load and execute individual software programs as and when required. The processor 50 also contains appropriate communications facilities, e.g. pins or pads (plus corresponding control software), for communicating as appropriate with other devices in the control unit 20, such as the pressure sensor 62.

The output device(s) 58 may provide visible, audio and/or haptic output. For example, the output device(s) 58 may include a speaker 58, a vibrator, and/or one or more lights. The lights are typically provided in the form of one or more light emitting diodes (LEDs), which may be the same or different colors (or multi-colored). In the case of multi-colored LEDs, different colors are obtained by switching different colored, e.g. red, green or blue, LEDs on, optionally at different relative brightnesses to give corresponding relative variations in color. Where red, green and blue LEDs are provided together, a full range of colors is possible, whilst if only two out of the three red, green and blue LEDs are provided, only a respective sub-range of colors can be obtained.

The output from the output device 58 may be used to signal to the user various conditions or states within the e-cigarette 10, such as a low battery warning. Different output signals may be used for signaling different states or conditions. For example, if the output device 58 is an audio speaker, different states or conditions may be represented by tones or beeps of different pitch and/or duration, and/or by providing multiple such beeps or tones. Alternatively, if the output device 58 includes one or more lights, different states or conditions may be represented by using different colors, pulses of light or continuous illumination, different pulse durations, and so on. For example, one indicator light might be utilized to show a low battery warning, while another indicator light might be used to indicate that the liquid reservoir 58 is nearly depleted. It will be appreciated that a given e-cigarette 10 may include output devices 58 to support multiple different output modes (audio, visual), etc.

The input device(s) 59 may be provided in various forms. For example, an input device (or devices) 59 may be implemented as buttons on the outside of the e-cigarette 10—e.g. as mechanical, electrical or capacitive (touch) sensors. Some devices may support blowing into the e-cigarette 10 as an input mechanism (such blowing may be detected by pressure sensor 62, which would then be also acting as a form of input device 59), and/or connecting/disconnecting the cartomizer 30 and control unit 20 as another form of input mechanism. Again, it will be appreciated that a given e-cigarette 10 may include input devices 59 to support multiple different input modes.

As noted above, the e-cigarette 10 provides an air path from the air inlet through the e-cigarette 10, past the pressure sensor 62 and the heater 310 in the cartomizer 30 to the mouthpiece 35. Thus when a user inhales on the mouthpiece 35 of the e-cigarette 10, the processor 50 detects such inhalation based on information from the pressure sensor 62. In response to such a detection, the CPU supplies power from the battery 54 to the 310, which thereby heats and vaporizes the nicotine from the liquid reservoir 38 for inhalation by the user.

In the particular implementation shown in FIG. 2, a FET 210 is connected between the battery 54 and the connector 21A. This FET 210 acts as a switch. The processor 50 is connected to the gate of the FET 210 to operate the switch, thereby allowing the processor 50 to switch on and off the flow of power from the battery 54 to heater 310 according to the status of the detected airflow. It will be appreciated that the heater current can be relatively large, for example, in the range 1-5 amps, and hence the FET 210 should be implemented to support such current control (likewise for any other form of switch that might be used in place of FET 210).

In order to provide more fine-grained control of the amount of power flowing from the battery 54 to the heater 310, a pulse-width modulation (PWM) scheme may be adopted. A PWM scheme may be based on a repetition period of say 1 ms. Within each such period, the switch 210 is turned on for a proportion of the period, and turned off for the remaining proportion of the period. This is parameterized by a duty cycle, whereby a duty cycle of 0 indicates that the switch is off for all of each period (i.e. in effect, permanently off), a duty cycle of 0.33 indicates that the switch is on for a third of each period, a duty cycle of 0.66 indicates that the switch is on for two-thirds of each period, and a duty cycle of 1 indicates that the FET 210 is on for all of each period (i.e. in effect, permanently on). It will be appreciated that these are only given as example settings for the duty cycle, and intermediate values can be used as appropriate.

The use of PWM provides an effective power to the heater 310 which is given by the nominal available power (based on the battery output voltage and the heater resistance) multiplied by the duty cycle. The processor 50 may, for example, utilize a duty cycle of 1 (i.e. full power) at the start of an inhalation to initially raise the heater 310 to its desired operating temperature as quickly as possible. Once this desired operating temperature has been achieved, the processor 50 may then reduce the duty cycle to some suitable value in order to supply the heater 310 with the desired operating power.

As shown in FIG. 2, the processor 50 includes a communications interface 55 for wireless communications, in particular, support for Bluetooth® Low Energy (BLE) communications.

Optionally the heater 310 may be utilized as an antenna for use by the communications interface 55 for transmitting and receiving the wireless communications. One motivation for this is that the control unit 20 may have a metal housing 202, whereas the cartomizer portion 30 may have a plastic housing 302 (reflecting the fact that the cartomizer 30 is disposable, whereas the control unit 20 is retained and therefore may benefit from being more durable). The metal housing 202 acts as a screen or barrier which can affect the operation of an antenna located within the control unit 20 itself. However, utilizing the heater 310 as the antenna for the wireless communications can help to avoid this metal screening because of the plastic housing of the cartomizer 30, but without adding additional components or complexity (or cost) to the cartomizer. Alternatively a separate antenna may be provided (not shown), or a portion of the metal housing 202 may be used.

If the heater 36 is used as an antenna then as shown in FIG. 2, the processor 50, more particularly the communications interface 55, may be coupled to the power line from the battery 54 to the heater 310 (via connector 31B) by a capacitor 220. This capacitive coupling occurs downstream of the switch 210, since the wireless communications may operate when the heater 310 is not powered for heating (as discussed in more detail below). It will be appreciated that capacitor 220 helps prevent the power supply from the battery 54 to the heater 310 being diverted back to the processor 50.

Note that the capacitive coupling may be implemented using a more complex LC (inductor-capacitor) network, which can also provide impedance matching with the output of the communications interface 55. (As known to the person skilled in the art, this impedance matching can help support proper transfer of signals between the communications interface 55 and the heater 310 acting as the antenna, rather than having such signals reflected back along the connection.)

In some implementations, the processor 50 and communications interface are implemented using a Dialog DA14580 chip from Dialog Semiconductor PLC, based in Reading, United Kingdom. Further information (and a data sheet) for this chip is available at www.dialog-semiconductor.com.

Figure 3:
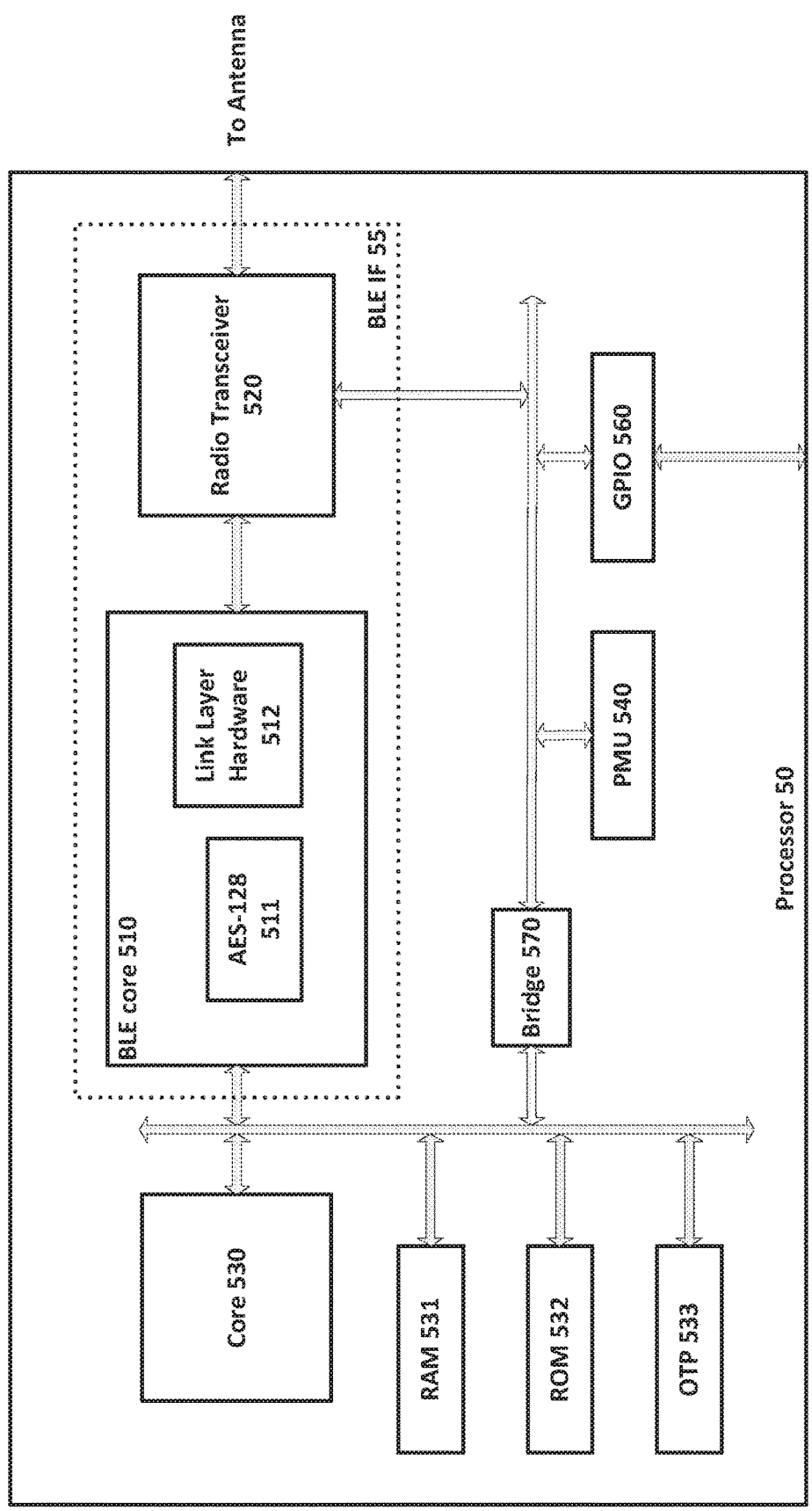
FIG. 3 is a simplified schematic diagram of the processor of the e-cigarette of FIG. 1 in accordance with some embodiments of the disclosure.

FIG. 3 presents a high-level and simplified overview of this chip 50, including the communications interface 55 for supporting Bluetooth® Low Energy. This interface includes in particular a radio transceiver 520 for performing signal modulation and demodulation, etc., link layer hardware 512, and an advanced encryption facility (128 bits) 511. The output from the radio transceiver 520 is connected to the antenna (for example, to the heater 310 acting as the antenna via capacitive coupling 220 and connectors 21A and 31B).

The remainder of processor 50 includes a general processing core 530, RAM 531, ROM 532, a one-time programming (OTP) unit 533, a general purpose I/O system 560 (for communicating with other components on the PCB 28), a power management unit 540 and a bridge 570 for connecting two buses. Software instructions stored in the ROM 532 and/or OTP unit 533 may be loaded into RAM 531 (and/or into memory provided as part of core 530) for execution by one or more processing units within core 530. These software instructions cause the processor 50 to implement various functionality described herein, such as interfacing with the sensor unit 61 and controlling the heater accordingly. Note that although the device shown in FIG. 3 acts as both a communications interface 55 and also as a general controller for the electronic vapor provision system 10, in other embodiments these two functions may be split between two or more different devices (chips)—e.g. one chip may serve as the communications interface 55, and another chip as the general controller for the electronic vapor provision system 10.

In some implementations, the processor 50 may be configured to prevent wireless communications when the heater 310 is being used for vaporizing liquid from reservoir 38. For example, wireless communications may be suspended, terminated or prevented from starting when switch 210 is switched on. Conversely, if wireless communications are ongoing, then activation of the heater 310 may be prevented—e.g. by disregarding a detection of airflow from the sensor unit 61, and/or by not operating switch 210 to turn on power to the heater 310 while the wireless communications are progressing.

One reason for preventing the simultaneous operation of heater 310 for both heating and wireless communications in some implementations is to help avoid potential interference from the PWM control of the heater 310. This PWM control has its own frequency (based on the repetition frequency of the pulses), albeit typically much lower than the frequency used for the wireless communications, and the two could potentially interfere with one another. In some situations, such interference may not, in practice, cause any problems, and simultaneous operation of heater 310 for both heating and wireless communications may be allowed (if so desired). This may be facilitated, for example, by techniques such as the appropriate selection of signal strengths and/or PWM frequency, the provision of suitable filtering, etc.

Figure 4:
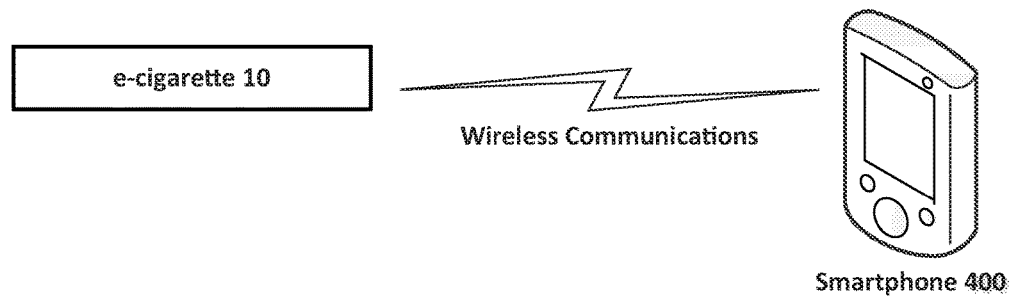
FIG. 4 is a schematic diagram of wireless communications between the e-cigarette of FIG. 1 and a mobile communication device.

FIG. 4 is a schematic diagram showing Bluetooth® Low Energy communications between an e-cigarette 10 and an application (app) running on a smartphone 400 or other suitable mobile communication device (tablet, laptop, smartwatch, etc.). Such communications can be used for a wide range of purposes, for example, to upgrade firmware on the e-cigarette 10, to retrieve usage and/or diagnostic data from the e-cigarette 10, to reset or unlock the e-cigarette 10, to control settings on the e-cigarette 10, etc.

In general terms, when the e-cigarette 10 is switched on, such as by using input device 59, or possibly by joining the cartomizer 30 to the control unit 20, it starts to advertise for Bluetooth® Low Energy communication. If this outgoing communication is received by smartphone 400, then the smartphone 400 requests a connection to the e-cigarette 10. The e-cigarette 10 may notify this request to a user via output device 58, and wait for the user to accept or reject the request via input device 59. Assuming the request is accepted, the e-cigarette 10 is able to communicate further with the smartphone 400. Note that the e-cigarette 10 may remember the identity of smartphone 400 and be able to accept future connection requests automatically from that smartphone 400. Once the connection has been established, the smartphone 400 and the e-cigarette 10 operate in a client-server mode, with the smartphone 400 operating as a client that initiates and sends requests to the e-cigarette 10 which therefore operates as a server (and responds to the requests as appropriate).

A Bluetooth® Low Energy link (also known as Bluetooth Smart®) implements the IEEE 802.15.1 standard, and operates at a frequency of 2.4-2.5 GHz, corresponding to a wavelength of about 12 cm, with data rates of up to 1 Mbit/s. The set-up time for a connection is less than 6 ms, and the average power consumption can be very low—of the order 1 mW or less. A Bluetooth® Low Energy link may extend up to some 50 m. However, for the situation shown in FIG. 4, the e-cigarette 10 and the smartphone 400 will typically belong to the same person, and will therefore be in much closer proximity to one another—e.g. 1 m. Further information about Bluetooth Low Energy can be found at www.bluetooth.com.

It will be appreciated that e-cigarette 10 may support other communications protocols for communication with smartphone 400 (or any other appropriate device). Such other communications protocols may be instead of, or in addition to, Bluetooth® Low Energy. Examples of such other communications protocols include Bluetooth® (not the low energy variant), see for example, www.bluetooth.com, near field communications (NFC), as per ISO 13157, and WiFi®. NFC communications operate at much lower wavelengths than Bluetooth (13.56 MHz) and generally have a much shorter range—say <0.2 m. However, this short range is still compatible with most usage scenarios such as shown in FIG. 4. Meanwhile, low-power WiFi® communications, such as IEEE802.11ah, IEEE802.11v, or similar, may be employed between the e-cigarette 10 and a remote device. In each case, a suitable communications chipset may be included on PCB 28, either as part of the processor 50 or as a separate component. The skilled person will be aware of other wireless communication protocols that may be employed in e-cigarette 10.

Figure 5:
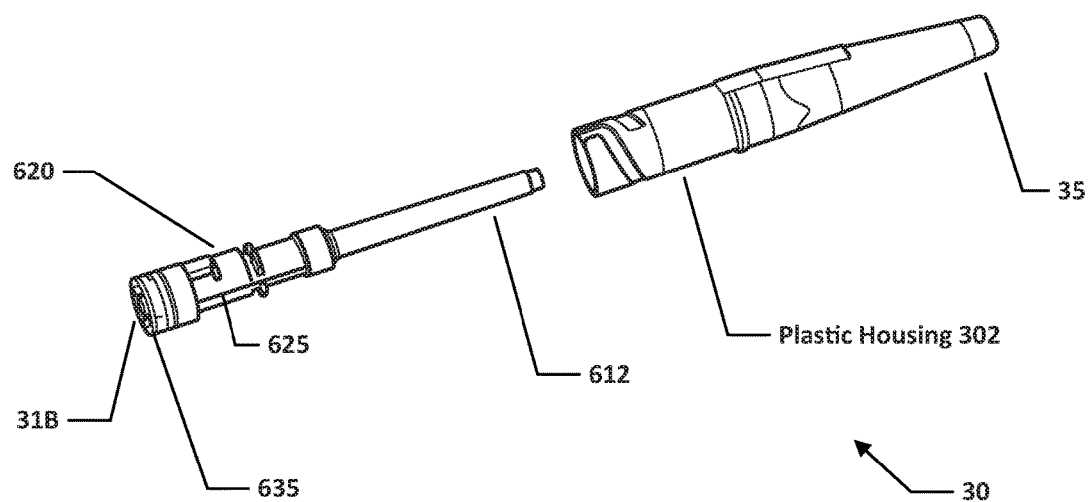
FIG. 5 is a schematic (exploded) diagram of the cartomizer of an e-cigarette in accordance with some embodiments of the disclosure.

FIG. 5 is a schematic, exploded view of an example cartomizer 30 in accordance with some embodiments. The cartomizer 30 has an outer plastic housing 302, a mouthpiece 35 (which may be formed as part of the housing), a vaporizer 620, a hollow inner tube 612, and a connector 31B for attaching to a control unit. An airflow path through the cartomizer 30 starts with an air inlet through connector 31B, then through the interior of vaporizer 625 and hollow tube 612, and finally out through the mouthpiece 35. The cartomizer 30 retains liquid in an annular region between (i) the plastic housing 302, and (ii) the vaporizer 620 and the inner tube 612. The connector 31B is provided with a seal 635 to help maintain liquid in this region and to prevent leakage.

Figure 6:
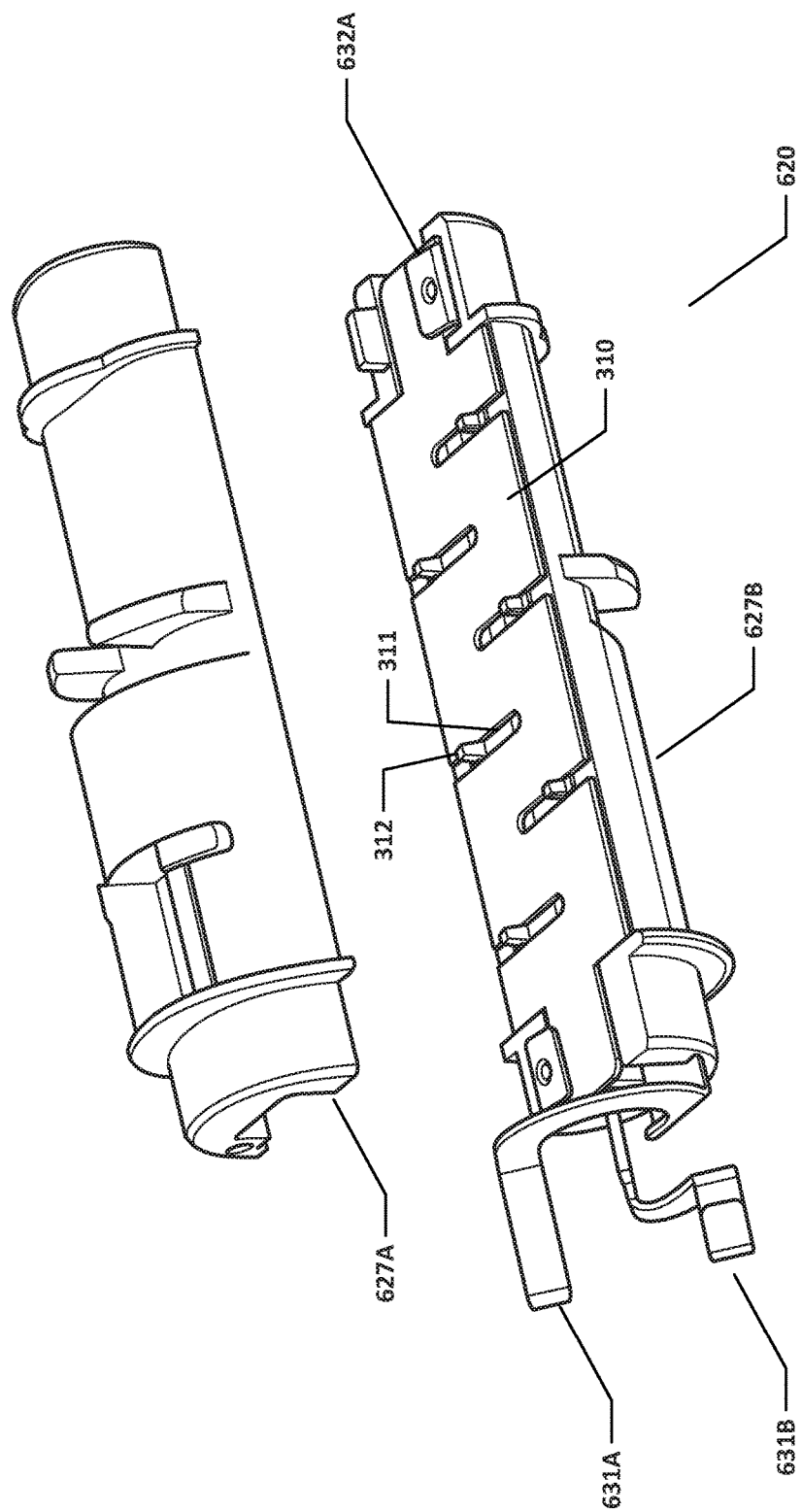
FIG. 6 is a schematic (exploded) diagram of the vaporizer from the cartomizer of FIG. 5 in accordance with some embodiments of the disclosure.

FIG. 6 is a schematic, exploded view of the vaporizer 620 from the example cartomizer 30 shown in FIG. 5. The vaporizer 620 has a substantially cylindrical housing (cradle) formed from two components, 627A, 627B, each having a substantially semi-circular cross-section. When assembled, the edges of the components 627A, 627B do not completely abut one another (at least, not along their entire length), but rather a slight gap 625 remains (as indicated in FIG. 5). This gap allows liquid from the outer reservoir around the vaporizer 620 and tube 612 to enter into the interior of the vaporizer 620.

One of the components 627B of the vaporizer 620 is shown in FIG. 6 supporting a heater 310. There are two connectors 631A, 631B shown for supplying power (and a wireless communication signal) to the heater 310. More particular, these connectors 631A, 631B link the heater 310 to connector 31B, and from there to the control unit 20. (Note that connector 631A is joined to pad 632A at the far end of vaporizer 620 from connector 31B by an electrical connection that passes under the heater 310 and which is not visible in FIG. 6.)

The heater 310 comprises a heating element formed from a sintered metal fiber material and is generally in the form of a sheet or porous, conducting material (such as steel). However, it will be appreciated that other porous conducting materials may be used. The overall resistance of the heating element in the example of FIG. 6 is around 1 ohm. However, it will be appreciated that other resistances may be selected, for example having regard to the available battery voltage and the desired temperature/power dissipation characteristics of the heating element. In this regard, the relevant characteristics may be selected in accordance with the desired aerosol (vapor) generation properties for the device depending on the source liquid of interest.

The main portion of the heating element is generally rectangular with a length (i.e. in a direction running between the connector 31B and the contact 632A) of around 20 mm and a width of around 8 mm. The thickness of the sheet comprising the heating element in this example is around 0.15 mm.

As can be seen in FIG. 6, the generally-rectangular main portion of the heating element has slots 311 extending inwardly from each of the longer sides. These slots 311 engage pegs 312 provided by vaporizer housing component 627B, thereby helping to maintain the position of the heating element in relation to the housing components 627A, 627B.

The slots 311 extend inwardly by around 4.8 mm and have a width of around 0.6 mm. The slots 311 extending inwardly are separated from one another by around 5.4 mm on each side of the heating element, with the slots extending inwardly from the opposing sides being offset from one another by around half this spacing. A consequence of this arrangement of slots 311 is that current flow along the heating element is in effect forced to follow a meandering path, which results in a concentration of current and electrical power around the ends of the slots 311. The different current/power densities at different locations on the heating element mean there are areas of relatively high current density that become hotter than areas of relatively low current density. This in effect provides the heating element with a range of different temperatures and temperature gradients, which can be desirable in the context of aerosol provision systems. This is because different components of a source liquid may aerosolize/vaporize at different temperatures, and so providing a heating element with a range of temperatures can help simultaneously aerosolize a range of different components in the source liquid.

The heater 310 shown in FIG. 6, having a substantially planar shape which is elongated in one direction, is well-suited to act as an antenna. In conjunction with the metal housing 202 of the control unit, the heater 310 forms an approximate dipole configuration, which typically has a physical size of the same order of magnitude as the wavelength of Bluetooth® Low Energy communications—i.e. a size of several centimeters (allowing for both the heater 310 and the metal housing 202) against a wavelength of around 12 cm.

Although FIG. 6 illustrates one shape and configuration of the heater 310 (heating element), the skilled person will be aware of various other possibilities. For example, the heater 310 may be provided as a coil or some other configuration of resistive wire. Another possibility is that the heater 310 is configured as a pipe containing liquid to be vaporized (such as some form of tobacco product). In this case, the pipe may be used primarily to transport heat from a place of generation (e.g. by a coil or other heating element) to the liquid to be vaporized. In such a case, the pipe still acts as a heater in respect of the liquid to be heated. Such configurations can again optionally be used as an antenna to support wireless configurations.

As was noted previously herein, a suitable e-cigarette 10 can communicate with a mobile communication device 400, for example by paring the devices using the Bluetooth® low energy protocol.

Consequently, it is possible to provide additional functionality to the e-cigarette 10 and/or to a system comprising the e-cigarette 10 and the smartphone 400, by providing suitable software instructions (for example in the form of an app) to run on the smartphone 400.

Figure 7:
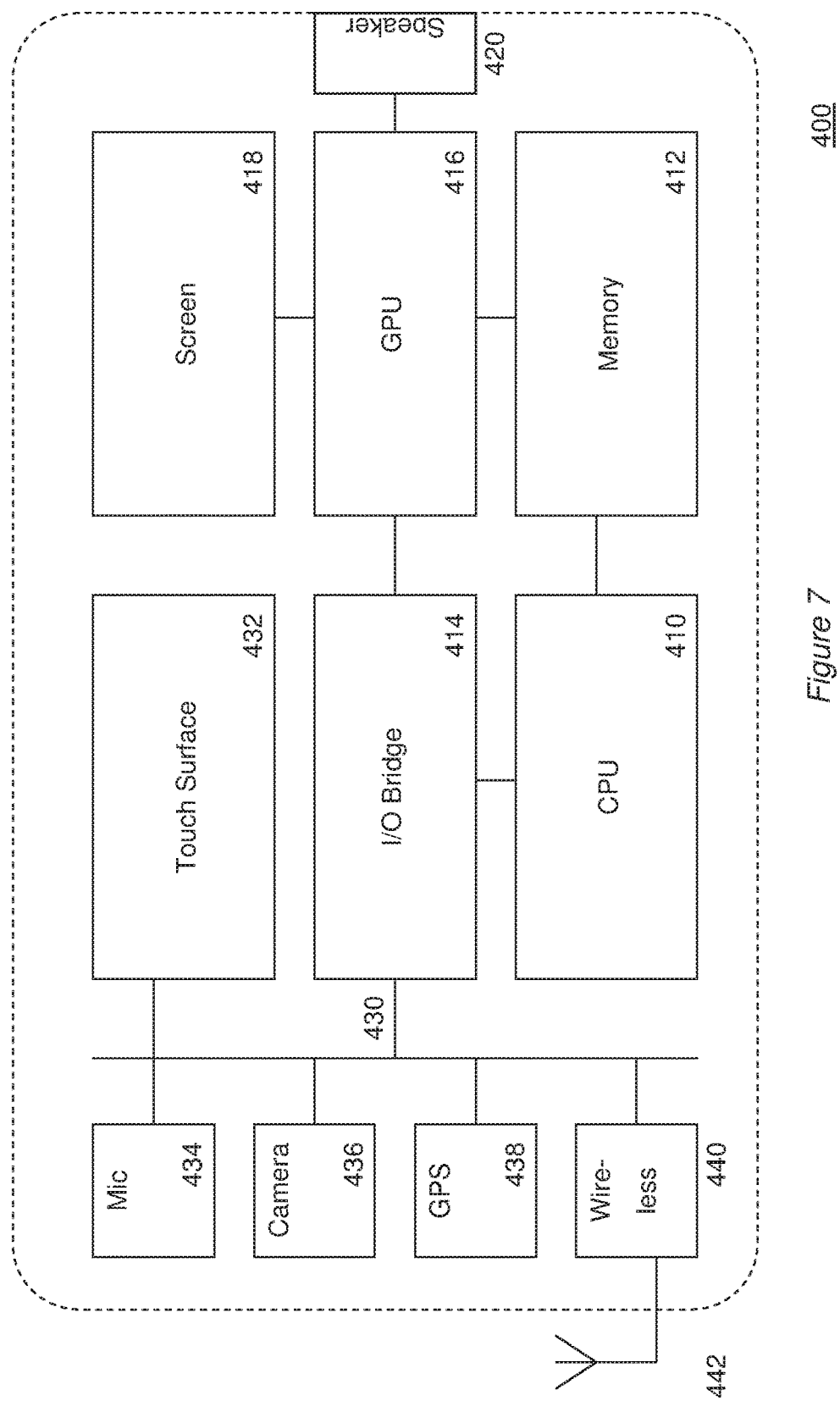
FIG. 7 is a schematic diagram of a mobile communication device in accordance with some embodiments of the disclosure.

Turning now to FIG. 7, a typical smartphone 400 comprises a central processing unit (CPU) (410). The CPU 410 may communicate with components of the smartphone 400 either through direct connections or via an I/O bridge 414 and/or a bus 430 as applicable.

In the example shown in FIG. 7, the CPU 410 communicates directly with a memory 412, which may comprise a persistent memory such as for example Flash® memory for storing an operating system and applications (apps), and volatile memory such as RAM for holding data currently in use by the CPU 410. Typically persistent and volatile memories are formed by physically distinct units (not shown). In addition, the memory 412 may separately comprise plug-in memory such as a microSD card, and also subscriber information data on a subscriber information module (SIM) (not shown).

The smartphone 400 may also comprise a graphics processing unit (GPU) 416. The GPU 416 may communicate directly with the CPU 410 or via the I/O bridge, or may be part of the CPU 410. The GPU 416 may share RAM with the CPU 410 or may have its own dedicated RAM (not shown) and is connected to the display 418 of the smartphone 400. The display is typically a liquid crystal (LCD) or organic light-emitting diode (OLED) display, but may be any suitable display technology, such as e-ink. Optionally the GPU 416 may also be used to drive one or more loudspeakers 420 of the smartphone 400.

Alternatively, the speaker may be connected to the CPU 410 via the I/O bridge and the bus. Other components of the smartphone 400 may be similarly connected via the bus, including a touch surface 432 such as a capacitive touch surface overlaid on the screen for the purposes of providing a touch input to the device, a microphone 434 for receiving speech from the user, one or more cameras 436 for capturing images, a global positioning system (GPS) unit 438 for obtaining an estimate of the geographical position of the smartphone 400, and wireless communication means 440.

The wireless communication means 440 may in turn comprise several separate wireless communication systems adhering to different standards and/or protocols, such as Bluetooth® (standard or low-energy variants), near field communication and Wi-Fi® as described previously, and also phone based communication such as 2G, 3G and/or 4G.

The systems are typically powered by a battery (not shown) that may be chargeable via a power input (not shown) that in turn may be part of a data link such as USB (not shown).

It will be appreciated that different smartphones may include different features (for example a compass or a buzzer) and may omit some of those listed above (for example a touch surface).

Thus more generally, in an embodiment of the present disclosure a suitable remote device such as smartphone 400 will comprise a CPU 410 and a memory 412 for storing and running an app, and wireless communication means operable to instigate and maintain wireless communication with the e-cigarette 10. It will be appreciated however that the remote device may be a device that has these capabilities, such as a tablet, laptop, smart TV or the like.

One example of additional functionality that may be provided to the e-cigarette 10 and/or to a combination of the e-cigarette 10 and the mobile communication device 400 is a method of synchronizing a feature between the e-cigarette 10 and the mobile communication device 400 of a user.

Figure 8:
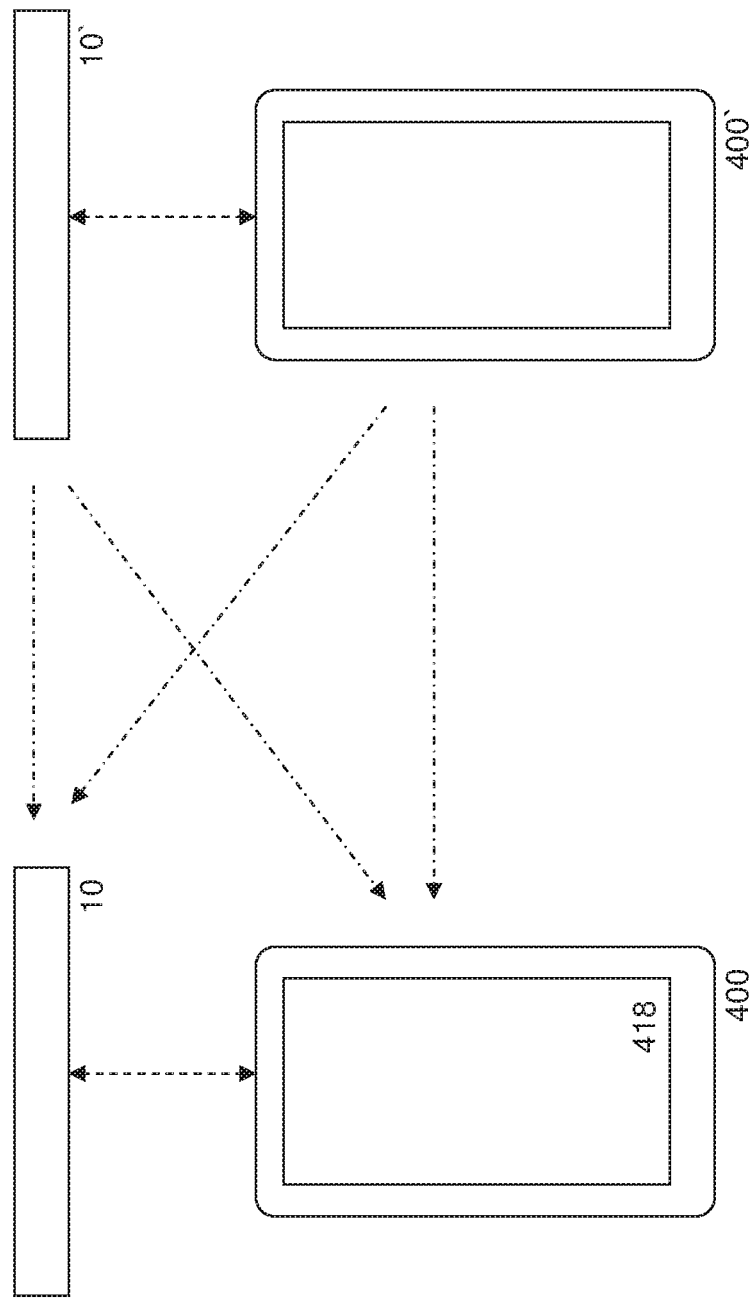
FIG. 8 is a schematic diagram of a feature synchronization system in accordance with some embodiments of the disclosure.
Figure 9:
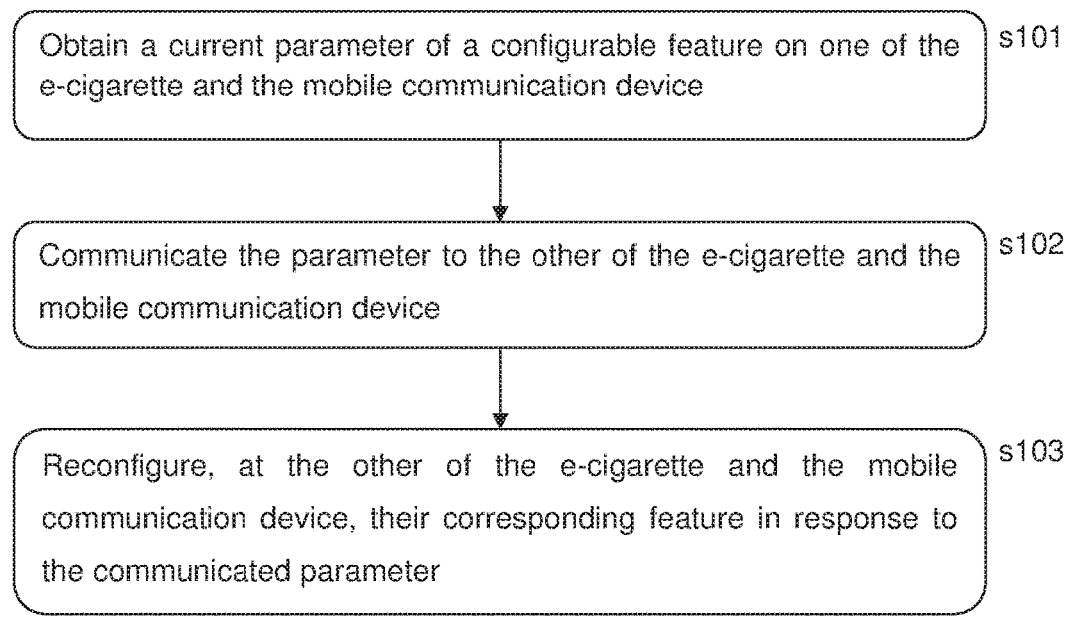
FIG. 9 is a flow diagram of a method of synchronizing a feature between an electronic vapor provision system and a mobile communication device of a first user in accordance with some embodiments of the disclosure.

Referring to FIGS. 8 and 9, a method of synchronizing a feature between an electronic vapor provision system and a mobile communication device of a first user comprises:

At s101, obtaining a current parameter of a configurable feature on one of the electronic vapor provision system and the mobile communication device.

It will be appreciated that a configurable feature may be obtained from either device, for example when the devices are first paired, or when the user uses an interface to modify a parameter or make a selection that has the result of modifying a parameter, or when an event occurs as the result of modifying a parameter.

In the case of an e-cigarette 10 that includes a multicolor LED as described previously herein, an example of a current parameter of a configurable feature that may originate with the e-cigarette 10 includes the current color of the LED (providing an "illuminated portion" of the e-cigarette).

Initially the color may be the default factory setting for the LED (the color may initially be randomly selected for each e-cigarette 10, or may correspond to a model type, for example), and this may be conveyed to the mobile communication device 400 upon first pairing. At other times, the current color may correspond to a warning status (for example "low battery" may correspond to one color whilst "low reservoir" may correspond to another), or may correspond to a color selection set using an input of the e-cigarette 10 (for example a button on the e-cigarette 10 may cycle through a predetermined number of colors to allow direct personalization by a user).

In this case, the processor 50 of the electronic vapor provision system is arranged to obtain the current parameter of the configurable feature of the electronic vapor provision system.

Conversely, in the case where the obtained current parameter of the configurable feature originates at the mobile communication device 400, the processor (CPU 410 of the mobile communication device 400) obtains the parameter. In this case the parameter may be a predominant color within a color theme of an app (for example colors in a menu bar, welcome screen, background region etc.,), a color theme of the operating system (again relating to colors in a menu bar, background region etc.,), an/or a predominant color of at least part of wallpaper image, such as a background image upon which app icons are overlaid during navigation. Hence the parameter may be a color setting of a feature of a graphical interface displayed on a color display of mobile communication device 400.

It will be appreciated that depending upon the capabilities of the e-cigarette 10, the configurable feature is not limited to the color of an LED. For example, where the e-cigarette 10 comprises a speaker 58, then obtain the current parameter of a configurable feature originating at the mobile communication device 400 may be a sound, for example a user-selected sound that is associated with an event, such as notifications. In this case the e-cigarette 10 may contain memory space for a sound sample, and the selected sound may be downloaded to the e-cigarette 10.

Similarly, the configurable feature may be time-variant; for example it may be an illumination pulse or variation signal, causing the brightness of an LED or graphical feature of the mobile communication device 400 to pulse or otherwise vary in a certain pattern, or change colors in a certain pattern; the signal can be transmitted to the e-cigarette 10 periodically, causing it to pulse in sync. Where appropriate a timing offset can be used to account for transmission delays between the mobile communication device 400 and the e-cigarette 10.

Optionally the illumination pulse signal may be responsive to a musical beat, in turn extracted for example using a low pass filter applied to a sound source such as an MP3 recording being played by the mobile communication device 400, or ambient sound detected by a microphone of the mobile communication device 400.

At s102, the method comprises communicating the parameter to the other of the electronic vapor provision system and the mobile communication device 400.

In the case where the parameter originates at the e-cigarette 10, communications interface 55 operates as a transmitter arranged to communicate the parameter to the mobile communication device 400.

The communication is provided in a format indicative that the mobile communication device 400 should reconfigure a corresponding feature in response to the communicated parameter; for example a predetermined flag or bit/byte sequence may be associated with the communication to indicate this.

Conversely in the case where the parameter originates at the mobile communication device 400, wireless transmitter 440 is arranged to communicate the parameter to the electronic vapor provision system. Again the communication is provided in a format indicative that the electronic vapor provision system should reconfigure its corresponding feature in response to the communicated parameter, again for example by use of a predetermined flag the incorporation of a predetermined bit/byte sequence within the communication.

As will be appreciated from the example given above, the parameter may comprise a single value where this can be appropriately interpreted by the processor of the corresponding device, or may comprise data for use by the processor of the corresponding device for example in the case of a sound sample.

At s103, the method comprises the other of the electronic vapor provision system and the mobile communication device 400 reconfiguring their corresponding feature in response to the communicated parameter.

Referring back to the examples above, where the originating parameter is an LED color of the e-cigarette 10, then a corresponding feature for the mobile communication device 400 may be one or more selected from the list consisting of a color theme of an app, a color theme of an operating system, and a color of at least part of a wallpaper image, or more generally a color setting of a feature of a graphical interface displayed on a color display of mobile communication device, much as described above for the case where the color parameter originates at the mobile communication device 400. Conversely where the user selects a color or theme for a graphical feature of a user interface of the mobile communication device 400, then the corresponding feature of the e-cigarette 10 may be the LED (or other indicator) color.

Typically the color can be expressed as a trio of values corresponding to red, green and blue levels, and these values are used to drive red green and blue sources of the multicolor LED at corresponding levels of brightness to create a composite color. Where the e-cigarette comprises a multicolor LED that does not cover a full color range/gamut (for example, the multicolor LED only comprises red and green sources, or only green and blue sources, or only blue and red sources or some other combination of colors, such as red, green and white), then the mobile communication device (or more specifically an app providing the functionality described herein) can be set to provide selectable colors within the capability of the multicolor LED of the e-cigarette 10.

Optionally, a color correction subsystem may be included in the mobile communication device 400, for example as part of the app. This color correction subsystem may use a color correction table and/or a color correction formula to modify the color parameters used for the e-cigarette LED when applied to the mobile communication device 400 display. This table and/or formula may be used to take account of differences in color range between the LED of the e-cigarette 10 and the display of the particular mobile communication device model; for example respective tables may be constructed empirically or based on product data for popular makes of mobile phone to visibly match the color of the display to the color of e-cigarette LED. Alternatively or in addition the table and/or formula may be used to take account of a current brightness setting of the mobile phone, for example by adding or subtracting an offset to the color parameter to visibly match an effective brightness of the e-cigarette LED.

Reducing the color variability between the e-cigarette LED and the mobile communication device display advantageously enables more colors to be distinctively selected; for example, a color selection based on a range of 16 values from minimum to maximum brightness in each color channel could be extended to a range of 32, 64, 128 or 256 values per channel.

It will be appreciated that by virtue of corresponding features between the e-cigarette 10 and the mobile communication device 400, optionally there may be reciprocal synchronization so that where a user manually alters an LED color on the e-cigarette (for example using a button or rotatable cuff on the device to cycle through a pre-set color selection), the corresponding parameter is transmitted to the mobile communication device 400 which updates the color of a feature of a displayed graphical interface; conversely if the user selects a feature of a displayed graphical interface that is part of the software environment operating according to the method (for example part of an app that provides enhanced functions and/or reporting for the e-cigarette 10), the corresponding parameter is transmitted to the e-cigarette 10, which updates the color of the LED accordingly.

Hence more generally wherever a corresponding feature exists between the e-cigarette 10 and the mobile communication device 400, whether this is based on lighting color, lighting timing, sounds or haptic feedback (e.g. vibration) then a parameter reflecting an aspect of a setting for a feature may be obtained from the electronic vapor provision system and communicated to the mobile communication device, or a parameter may be obtained from the mobile communication device 400 and communicated to the electronic vapor provision system.

Further examples of parameters that may be obtained from either device, depending on circumstances, include system settings such as the strength or vapor provision level of the e-cigarette 10 which may be set on the device or remotely via the mobile communication device 400; where this occurs a corresponding LED color, or pulse rate or sound may be used to indicate the strength and the associated parameter may be synchronized between the devices.

Similarly the respective type of liquid being used for vaporization (for example the flavor) may be indicated by a color or sound that can be synchronized. Where the e-cigarette 10 and the reservoir are arranged so that the reservoir can indicate the type of contents to the e-cigarette, then the e-cigarette 10 may select a corresponding LED color and transmits this color parameter to the mobile communication device. Alternatively where either the reservoir does not indicate the type of content or the e-cigarette 10 cannot detect this, then the user may manually select a flavor via a menu on the mobile communication device app; the mobile communication device 400 may then select a corresponding LED color and transmit this parameter to the e-cigarette 10. In either case, the color scheme serves to act as a reminder to the user, particularly if, for convenience, the user has multiple e-cigarettes of a similar make each loaded with different flavor e-liquids.

It will be appreciated that in the case that a user has multiple e-cigarettes 10 paired with a single mobile communication device 400, the mobile communication device 400 may maintain a plurality of corresponding profiles, so that parameters are kept distinct for each e-cigarette 10. Where more than one paired e-cigarette 10 is in communication with the mobile communication device 400, the mobile communication device 400 may select a profile on the basis of which e-cigarette 10 has been most recently used, and synchronize with that e-cigarette 10.

The above example embodiments can thus allow a user to personalize their e-cigarette system comprising both the e-cigarette 10 and their mobile phone 400 (e.g. the appearance of a user interface of an app running on the mobile phone 400). This personalization may comprise the selection of default colors and/or sounds for normal use of the e-cigarette 10 and/or for various warnings (e.g. low battery, low reservoir).

Such personalization can be helpful particularly where multiple users with similar e-cigarette devices are likely to mingle; for example where a couple have respective e-cigarettes 10 and wish to identify their own for use at the start of the day, or where at a bar or club several people place their e-cigarettes on a table and wish to disambiguate ownership.

Conversely, such personalization can be used in the opposite manner for social purposes; for example a group of friends may choose to select a particular color that they all use.

Figure 10:
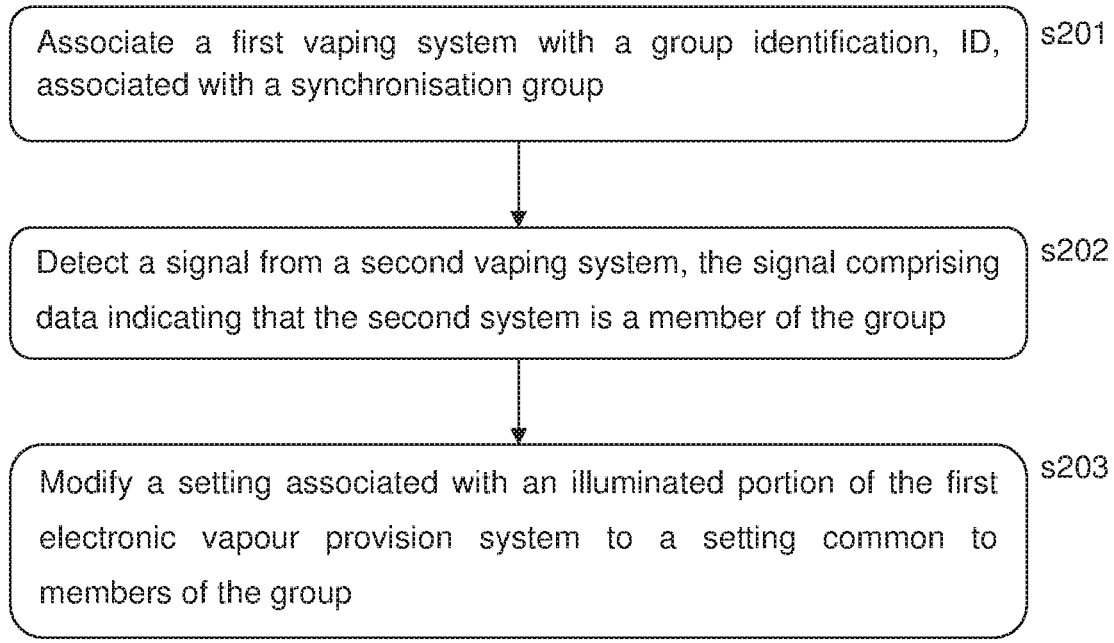
FIG. 10 is a flow diagram of a method of synchronizing a feature between two vaping systems in accordance with some embodiments of the disclosure.

With regards to this usage, referring again to FIG. 8 and now also FIG. 10, in an embodiment of the present disclosure the mobile communication device 400 may be adapted to facilitate the synchronization of one or more parameters of the e-cigarette 10 and optionally mobile communication device 400 of a first user with the e-cigarette 10' and optionally mobile communication device 400' of a second or further users.

Accordingly, referring to FIGS. 8 and 10, a method of synchronizing a feature between a first vaping system comprising a first electronic vapor provision system and a second vaping system comprising a second electronic vapor provision system, wherein the first and second vaping systems are members of a synchronization group, comprises:

At s201, associating the first vaping system with a group identification, ID, associated with the synchronization group;

At s202, detecting a signal from the second vaping system, the signal comprising data indicating that the second vaping system is a member of the group; and At s203, modifying a setting associated with an illuminated portion of the first electronic vapor provision system to a setting common to members of the group.

Here, a "vaping system" may comprise an electronic vapor provision system (i.e. an e-cigarette) alone, or a combination of an e-cigarette and a mobile communication device (i.e. a mobile phone running a suitable app).

If the first vaping system only comprises a first electronic vapor provision system, then the first electronic vapor provision system may comprise a memory to store the group ID (such as a memory associated with processor 50), a receiver (such as communications interface 55) arranged to receive the signal, and a processor (such as processor 50) arranged to verify the data indicating that the second vaping system is a member of the same group, and if so to modify the setting if the data is verified. In this case the verification may comprise comparing the stored group ID to a group ID included in the received signal.

Meanwhile if the first vaping system also comprises a first mobile communication device paired to the first electronic vapor provision system, then the first mobile communication device may comprise a memory 412 arranged to store the group ID, a receiver 440 arranged to receive the signal, a processor 410 arranged to verify the data indicating that the second vaping system is a member of the same group; and a transmitter arranged to transmit instructions to the first electronic vapor provision system to modify a setting of an illuminated portion of the first electronic vapor provision system if the data is verified. As previously described herein, this transmission may comprise an indication, e.g. be in a format, that indicates that the first electronic vapor provision system should reconfigure the setting of the illuminated portion in response to the communicated modification to the setting. Optionally also as described previously, the mobile communication device will modify a corresponding feature of its graphical user interface.

In the case where the first vaping system also comprises a first mobile communication device, the verification may be more sophisticated than simply comparing the stored group ID to a group ID included in the received signal. For example the received signal may comprise a token that the second vaping system received from a trusted server (not shown). The first mobile communication device may then send the token and the locally stored group ID to the server, which returns data indicating whether or not the token and the group ID are validly associated at the server. In this way neither vaping system needs to broadcast the group ID in order to for the first vaping system to establish that it belongs to the same group as the second vaping system. This provides a more secure means of synchronizing e-cigarettes within groups.

Correspondingly, if the second vaping system only comprises a second electronic vapor provision system 10', then the second electronic vapor provision system should comprise a memory comprising data indicating that the second vaping system is a member of a group (for example the group ID or a token), and a transmitter (such as communications interface 55) arranged to broadcast a signal to the remote first vaping system comprising a first electronic vapor provision system, the signal comprising data indicating that the second vaping system is a member of the group. The group ID or token may have been previously transmitted to the second electronic vapor provision system by a paired second mobile communication device that is subsequently not present as part of the second vaping system in this instance.

This transmitted signal may then be received by the first vaping system (i.e. the first electronic vapor provision system and/or the first mobile communication device).

Meanwhile, if the second vaping system does also comprise a second mobile communication device 400' then it may comprise a memory 412 comprising data indicating that the second vaping system is a member of a group (for example a group ID and/or a token received from a trusted server, for example upon registration to a grouping service), and a transmitter 410 arranged to broadcast a signal to the remote first vaping system comprising a first electronic vapor provision system, the signal comprising the data indicating that the second vaping system is a member of the group.

Hence, independent of the composition of the first vaping system or the second vaping system, where two or more such e-cigarettes (or their paired mobile communication device(s), as applicable) are within a wireless range, then an illuminated region of the e-cigarette synchronizes in a similar manner to that described previously herein, such as for example selecting a common color or selecting a common time variation in brightness or color. It will be appreciated that the color or time variation above may be pre-defined for the group, either as a factory setting or as a value that can be extracted from the group ID itself, or where applicable is obtained from the trusted server. Alternatively, the modification to the color or time setting may be transmitted by the second vaping system and received from it by the first vaping system, allowing the second user to select a color or time setting of their choice. This may be advantageous where a default or previously set color or time setting does not appear sufficiently distinct within a crowd of other users; for example if the default or previously selected color was red, and a user entered a bar where a significant number of other users already had electronic vapor provision systems with red lights, then the user may select a notably different color for the group, enabling clear identification of group members.

Examples of who group members may be (who hence commonly hold the group ID) include comprise e-cigarettes from the same manufacturer, e-cigarettes of the same model, and e-cigarettes holding the same e-liquid. In this latter case as noted previously the liquid reservoir may automatically inform the e-cigarette of its contents or this may be entered via a selection mechanism of an app on the mobile communication device. Subsequently the user may easily find other users of the same liquid because these e-cigarettes all change to the same color light or time sequence when in proximity to each other. Where the liquid comprises a specific flavor this may be advantageous as it allows users of specific flavors to group together and avoid mixing odors.

Another example of a group is a mobile communication device running a particular app. In this case the app holds the group ID and optionally a token associated with the group ID. In a first instance any mobile communication device running the app is a member of the app's group. In another instance the app enables users to register as social groups. In this way a group of friends may associate themselves as a group so that their e-cigarettes display a synchronized color and/or timing behavior when they are in proximity to each other.

Such an app may have a group set-up mode arranged to detect broadcast IDs from friend's e-cigarettes or associated mobile phones, and these may subsequently be used as tokens indicative of membership the group; at the same time a group ID is shared amongst group members. Alternatively where the friends are not in proximity for direct communication when setting up the group, this may be done via a remote trusted server to generate a group ID and tokens for use as described previously herein.

A group ID may be a single-use group ID. Hence a further example of a group is two or more users sharing a single use group ID. For example, a dating website may, amongst other contact information, automatically include a group ID (and optionally a token if server verification is to be used). Subsequently at a bar or other establishment the two users, who may not have previously met in person, may recognize each other by virtue of synchronized colors and/or variations in brightness and/or color of their e-cigarettes, and optionally also a graphical feature of their mobile phones. This provides a discreet means of recognizing someone in a potentially crowded environment.

The single use group ID may be subsequently discarded (i.e. removed from the memory of the electronic vapor provision system and/or mobile communication device, or similarly from the trusted server). Alternatively or in addition to discarding the group ID when a second vaping system is verified as belonging to the same group as a first vaping system, such a single use group ID may also be discarded if a predetermined time period has elapsed.

It will be appreciated that a vaping system can be the member or potential member of more than one group at the same time, such as for example separate groups of friends, a couple, an app and an e-liquid group. Optionally a user can select to actively participate in a group, for example by using on/off settings in an app. Optionally the settings can be communicated to a paired and suitably capable e-cigarette, enabling the e-cigarette to operate independently of the mobile phone as a vaping system if necessary.

It will also be appreciated that a vaping system can simultaneously be a first vaping system and a second vaping system as described herein, both transmitting data indicative of a group membership and also attempting to detect such data from other devices. Hence where to such devices come into range they may both receive data from each other and each separately verify membership of the other device as being in the same group. Where setting modification data is also transmitted, then where the modification is pre-set, either as a factory setting or as a setting predetermined by the group, then it would not matter if each vaping system adopts the setting modification data of the other as they are the same. However where these are different for some reason, then optionally the most recently changed setting modification data takes precedence. To facilitate this, a timestamp or version number may be associated with the setting modification data. Alternatively a prime group member may be preselected during group set up whose setting modification data takes precedence. Similarly membership joining order may be used to set precedence.

It will be appreciated that the any of the methods described herein may be carried out on conventional hardware suitably adapted as applicable by software instruction or by the inclusion or substitution of dedicated hardware.

Thus the required adaptation to existing parts of a conventional equivalent device may be implemented in the form of a computer program product comprising processor implementable instructions stored on a tangible non-transitory machine-readable medium such as a floppy disk, optical disk, hard disk, PROM, RAM, flash memory or any combination of these or other storage media, or realized in hardware as an ASIC (application specific integrated circuit) or an FPGA (field programmable gate array) or other configurable circuit suitable to use in adapting the conventional equivalent device. Separately, such a computer program may be transmitted via data signals on a network such as an Ethernet, a wireless network, the Internet, or any combination of these of other networks.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc other than those specifically described herein. The disclosure may include other inventions not presently claimed, but which may be claimed in future.

The invention claimed is:

1. A method of synchronizing a feature between an electronic vapor provision system and a mobile communication device of a user, the method comprising:
   obtaining a current parameter of a configurable feature on one of the electronic vapor provision system or the mobile communication device;
   communicating an indication of the current parameter to the other of the electronic vapor provision system or the mobile communication device; and
   the other one of the electronic vapor provision system or the mobile communication device reconfiguring a corresponding configurable feature in response to the communicated indication of the current parameter,
   wherein the configurable feature of the electronic vapor provision system is a color of an illuminated portion of the electronic vapor provision system,
   and wherein the configurable feature of the mobile communication device is one or more selected from the group consisting of:
      i. a color theme of an app;
      ii. a color theme of an operating system; and
      iii. a color of at least part of a wallpaper image.

2. The method of claim 1, further comprising:
   using a color correction subsystem at the mobile communication device to modify at least one of a color or a brightness associated with the current parameter for which the indication is communicated to match at least one of a color or a brightness of a feature displayed on the mobile communication device display to the illuminated portion of the electronic vapor provision system.

3. The method of claim 1, wherein the color corresponds to a respective type of liquid for vaporization by the electronic vapor provision system.

4. The method of claim 1, wherein the color corresponds to a selected vapor provision level for the electronic vapor provision system.

5. The method of claim 1, wherein the current parameter is obtained from the electronic vapor provision system and communicated to the mobile communication device.

6. The method of claim 1, wherein the current parameter is obtained from the mobile communication device and communicated to the electronic vapor provision system.

7. A non-transitory computer-readable storage medium storing a computer program product which, when read by a computer, causes the computer to implement the method of claim 1.

8. An electronic vapor provision system, comprising:
   a processor arranged to obtain a current parameter of a configurable feature of the electronic vapor provision system;
   a transmitter arranged to communicate an indication of the current parameter to a mobile communication device in association with an indication the mobile communication device should reconfigure a corresponding feature in response to the communicated indication of the current parameter; and
   a multicolor LED;
   wherein the configurable feature is a color setting of the multicolor LED,
   and wherein the corresponding feature of the mobile communication device is one or more selected from the group consisting of:
      i. a color theme of an app;
      ii. a color theme of an operating system; and
      iii. a color of at least part of a wallpaper image.

9. The electronic vapor provision system of claim 8, wherein:
   the color setting of the multicolor LED is responsive to one or more selected from the group consisting of:
      i. a default factory setting;
      ii. a warning status;
      iii. a color selection set using an input of the electronic vapor provision system; and
      iv. a detected other electronic vapor provision system.

10. A mobile communication device, comprising:
   a color display;
   a processor arranged to obtain a current parameter of a configurable feature of the mobile communication device;
   a transmitter arranged to communicate an indication of the current parameter to an electronic vapor provision system in association with an indication the electronic vapor provision system should reconfigure a corresponding feature in response to the communicated current parameter,
   wherein the corresponding feature of the electronic vapor provision system is a color of an illuminated portion of the electronic vapor provision system,
   and wherein the configurable feature of the mobile communication device is one or more selected from the group consisting of:
      i. a color theme of an app;
      ii. a color theme of an operating system; and
      iii. a color of at least part of a wallpaper image.

11. The mobile communication device of claim 10, further comprising:
   a receiver arranged to receive a communication from a third-party device comprising a current parameter of a configurable feature relating to one of an electronic vapor provision system or a mobile communication device of another user.

* * * * *